United States Patent
King et al.

(10) Patent No.: US 12,004,831 B2
(45) Date of Patent: Jun. 11, 2024

(54) SURGICAL ROBOTIC SYSTEM INCLUDING SYNCHRONOUS AND ASYNCHRONOUS NETWORKS AND A METHOD EMPLOYING THE SAME

(71) Applicant: Covidien LP, Mansfield, MA (US)

(72) Inventors: Daniel R. King, Jacksonville, FL (US); Samir A. Zahine, Billerica, MA (US); Nuno Almeida, Cambridge, MA (US)

(73) Assignee: COVIDIEN LP, Mansfield, MA (US)

( * ) Notice: Subject to any disclaimer, the term of this patent is extended or adjusted under 35 U.S.C. 154(b) by 992 days.

(21) Appl. No.: 16/937,808

(22) Filed: Jul. 24, 2020

(65) Prior Publication Data

US 2020/0352664 A1 Nov. 12, 2020

Related U.S. Application Data

(63) Continuation of application No. PCT/US2019/016224, filed on Feb. 1, 2019, and a
(Continued)

(51) Int. Cl.
*A61B 34/37* (2016.01)
*A61B 34/00* (2016.01)
(Continued)

(52) U.S. Cl.
CPC .............. *A61B 34/37* (2016.02); *G16H 30/40* (2018.01); *H04L 7/027* (2013.01); *A61B 34/25* (2016.02); *A61B 34/76* (2016.02)

(58) Field of Classification Search
CPC .......... A61B 34/30; A61B 34/35; A61B 34/37
See application file for complete search history.

(56) References Cited

U.S. PATENT DOCUMENTS 7,757,028 B2 7/2010 Druke et al.
7,818,647 B2 10/2010 Lohr et al.
(Continued)

OTHER PUBLICATIONS

Australian Examination Report No. 1 dated Feb. 11, 2021 corresponding to counterpart Patent Application AU 2020210243.
(Continued)

*Primary Examiner* — Christopher A Flory
(74) *Attorney, Agent, or Firm* — Carter, DeLuca & Farrell, LLP

(57) ABSTRACT

Surgical robotic systems including synchronous and asynchronous networks and methods employing the same are provided. One surgical robotic system includes a networked computing node, a slave robot assembly, and first and second communication paths. The slave robot assembly includes subunits, communicatively coupled to one another by way of the first communication paths, thereby forming at least a portion of a synchronous network. The networked computing node and a subunit are communicatively coupled to one another by way of the second communication paths, thereby forming at least a portion of a second network, and are configured to communicate one or more packets to one another by way of the second network. The subunit is configured to communicate, with the other subunits via the synchronous network, data from the one or more packets. A clock rate of the synchronous network is independent from a clock rate of the second network.

18 Claims, 6 Drawing Sheets

Related U.S. Application Data continuation of application No. PCT/US2019/016229, filed on Feb. 1, 2019.

(60) Provisional application No. 62/625,683, filed on Feb. 2, 2018, provisional application No. 62/625,667, filed on Feb. 2, 2018.

(51) Int. Cl.
*G16H 30/40* (2018.01)
*H04L 7/027* (2006.01)

(56) References Cited

U.S. PATENT DOCUMENTS

| | | | |
|---|---|---|---|
| 9,339,343 B2 | 5/2016 | Swarup et al. | |
| 9,408,668 B2 | 8/2016 | Durant et al. | |
| 9,446,517 B2 | 9/2016 | Burns et al. | |
| 2007/0086487 A1 | 4/2007 | Yasuda et al. | |
| 2007/0150631 A1 | 6/2007 | Druke et al. | |
| 2007/0156285 A1 | 7/2007 | Sillman et al. | |
| 2008/0098065 A1 | 4/2008 | Lee et al. | |
| 2010/0010671 A1 | 1/2010 | Miyamoto | |
| 2013/0184699 A1* | 7/2013 | Behnke, II | A61B 18/18 606/33 |
| 2014/0324070 A1 | 10/2014 | Min et al. | |
| 2015/0112481 A1* | 4/2015 | Burns | B25J 9/1674 700/248 |
| 2015/0149426 A1 | 5/2015 | Kim et al. | |
| 2015/0341246 A1 | 11/2015 | Boubez | |
| 2017/0161893 A1* | 6/2017 | Carnes | G06T 19/006 |
| 2018/0338806 A1* | 11/2018 | Grubbs | A61B 34/30 |
| 2020/0078096 A1 | 3/2020 | Barbagli et al. | |
| 2020/0305945 A1* | 10/2020 | Morgan | H04R 29/001 |
| 2023/0226271 A1* | 7/2023 | Lanigan | A61M 5/14244 604/406 |

OTHER PUBLICATIONS

Extended European Search Report dated Oct. 5, 2021 corresponding to counterpart Patent Application EP 19746911.7.

Extended European Search Report dated Oct. 13, 2021 corresponding to counterpart Patent Application EP 19748231.8.

Chinese Office Action dated May 17, 2023 for Chinese Patent Application No. 201980017905.0 (31 Pages).

International Search Report dated May 15, 2019 and Written Opinion completed May 14, 2019 corresponding to counterpart Int'l Patent Application PCT/US2019/016224.

International Search Report dated May 16, 2019 and Written Opinion completed May 15, 2019 corresponding to counterpart Int'l Patent Application PCT/US2019/016229.

Bzostek A., et al: "Distributed Modular Computer-Integrated Surgical Robotic Systems: Implementation Using Modular Software and Networked Systems". In: Delp S.L., DiGoia A.M., Jaramaz B. (eds) Medical Image Computing and Computer-Assisted Intervention—MICCAI 2000. Lecture Notes in Computer Science, vol. 1935. Springer, Berlin, Heidelberg. https://doi.org/10.1007/978-3-540-40899-4_101.

Indian Office Action dated May 30, 2022 corresponding to counterpart Patent Application IN 202017033743.

\* cited by examiner

SURGICAL ROBOTIC SYSTEM INCLUDING SYNCHRONOUS AND ASYNCHRONOUS NETWORKS AND A METHOD EMPLOYING THE SAME

CROSS-REFERENCE TO RELATED APPLICATIONS

This application is a Continuation Application of PCT Application Serial No. PCT/US2019/016224, filed Feb. 1, 2019, which claims benefit of and priority to U.S. Provisional Patent Application Ser. No. 62/625,667 filed Feb. 2, 2018, the disclosures of each of the above-identified applications are hereby incorporated by reference in their entirety.

This application is also a Continuation Application of PCT Application Serial No. PCT/US2019/016229, filed Feb. 1, 2019, which claims benefit of and priority to U.S. Provisional Patent Application Ser. No. 62/625,683 filed Feb. 2, 2018, the disclosures of each of the above-identified applications are hereby incorporated by reference in their entirety.

BACKGROUND

With surgical robotic systems growing in popularity, efforts are underway to develop improved surgical robotic systems that have enhanced capabilities, performance, and flexibility and that can accommodate a wide range of surgical procedures. Some surgical robotic systems under development include multiple subsystems, which communicate with one another over various communication links. As the complexity of surgical robotic systems increases, so do the challenges involved with ensuring that surgical robotic systems operate and/or communicate in an efficient manner, for instance, that mitigates various types of latency.

SUMMARY

The present disclosure relates to robotic systems, and more particularly, to surgical robotic systems including synchronous and asynchronous networks and communication methods employing the synchronous and asynchronous networks.

According to an aspect of the present disclosure, systems and methods are provided that address the above mentioned needs. In an aspect of the present disclosure, a surgical robotic system is provided. The system includes a networked computing node, a slave robot assembly, a plurality of first communication paths, and a plurality of second communication paths. The slave robot assembly includes a plurality of subunits. The plurality of subunits are communicatively coupled to one another by way of the plurality of first communication paths, thereby forming at least a portion of a synchronous network. The networked computing node and at least one of the plurality of subunits are communicatively coupled to one another by way of one or more of the plurality of second communication paths, thereby forming at least a portion of a second network, and are configured to communicate one or more packets to one another by way of the second network. The at least one of the plurality of subunits is configured to communicate, with other ones of the plurality of subunits by way of the synchronous network, data from the one or more packets. A clock rate of the synchronous network is independent from a clock rate of the second network. The networked computing node further includes a global safety monitor and the slave robot assembly includes a memory that stores one or more local resolution rules. The at least one of the plurality of subunits is further configured to (1) receive a safety alert from another subunit of the plurality of subunits, by way of one or more of the plurality of first communication paths, (2) determine whether a safety metric of the received safety alert exceeds a respective threshold, (3) in response to determining that the safety metric exceeds the respective threshold, determine, based on the one or more local resolution rules, whether an action relating to the corresponding safety alert can be performed by one or more of the plurality of subunits, (4) in response to determining that the action relating to the corresponding safety alert can be performed by one or more of the plurality of subunits, cause the action to be performed by one or more of the plurality of subunits to address the safety alert, and (5) in response to determining that the action relating to the corresponding safety alert cannot be performed by any of the plurality of subunits, transmit, by way of the second network, the safety alert to the global safety monitor.

In another aspect of the present disclosure, the one or more local resolution rules include at least one of information indicating one or more actions corresponding to safety alerts, respectively, or information indicating whether one or more of the plurality of subunits of the slave robot assembly can perform the one or more actions corresponding to the safety alerts, respectively.

In yet another aspect of the present disclosure, the action includes powering down one or more of the plurality of subunits that are associated with the safety alert.

In still another aspect of the present disclosure, the global safety monitor of the networked computing node is further configured to receive the safety alert from the one of the plurality of subunits by way of one or more of the plurality of second communication paths, and, in response to the receiving of the safety alert, cause the networked computing node to perform the action to address the safety alert.

In a further aspect of the present disclosure, each of the plurality of subunits is configured to transmit a corresponding safety alert to the global safety monitor by way of a respective path including at least one of (a) the one or more of the plurality of second communication paths or (b) one or more of the plurality of first communication paths, another one of the plurality of subunits, and the one or more of the plurality of second communication paths.

In another aspect of the present disclosure, the surgical robotic system further comprises a surgeon console, wherein the surgeon console, the networked computing node, and the at least one of the plurality of subunits are communicatively coupled to one another by way of one or more of the plurality of second communication paths, thereby forming at least another portion of the second network.

In yet another aspect of the present disclosure, the plurality of subunits are communicatively coupled to each other, by way of the plurality of first communication paths, in a ring topology.

In still another aspect of the present disclosure, the surgical robotic system further comprises a second slave robot assembly, including a plurality of second subunits, and a plurality of third communication paths. The plurality of second subunits are communicatively coupled to one another by way of the plurality of third communication paths, thereby forming at least a portion of a second synchronous network. A clock rate of the second synchronous network is independent from the clock rate of the synchronous network and from the clock rate of the second network.

In a further aspect of the present disclosure, the slave robot assembly is associated with a first unique identifier and the second slave robot assembly is associated with a second unique identifier.

In another aspect of the present disclosure, the one or more packets include the first unique identifier associated with the slave robot assembly or the second unique identifier associated with the second slave robot assembly.

In yet another aspect of the present disclosure, the second network is a synchronous network.

In still another aspect of the present disclosure, the second network is an asynchronous network.

In accordance with another aspect of the present disclosure, a method of employing a synchronous network and an asynchronous network of a surgical robotic system is provided. The method comprises storing one or more local resolution rules in a memory of a slave robot assembly. A safety alert is received, by at least one of a plurality of subunits of the slave robot assembly, from another subunit of the plurality of subunits, by way of the synchronous network. A determination is made as to whether a safety metric of the received safety alert exceeds a respective threshold. In response to a determination that the safety metric exceeds the respective threshold, a determination is made, based on the one or more local resolution rules, as to whether an action relating to the corresponding safety alert can be performed by one or more of the plurality of subunits. In response to a determination that the action relating to the corresponding safety alert can be performed by one or more of the plurality of subunits, the action is caused to be performed by one or more of the plurality of subunits to address the safety alert. In response to a determination that the action relating to the corresponding safety alert cannot be performed by any of the plurality of subunits, the safety alert is transmitted, by way of the asynchronous network, to a global safety monitor in a networked computing node. A clock rate of the synchronous network is independent from a clock rate of the asynchronous network.

In another aspect of the present disclosure, the one or more local resolution rules include information indicating one or more actions corresponding to safety alerts, and/or information indicating whether one or more of the subunits of the slave robot assembly can perform the one or more actions corresponding to the safety alerts.

In yet another aspect of the present disclosure, the action includes powering down one or more of the plurality of subunits that are associated with the safety alert.

In still another aspect of the present disclosure, the method further comprises receiving the safety alert from the one of the subunits by way of the asynchronous network, and, in response to the receiving of the safety alert, causing the networked computing node to perform the action to address the safety alert.

In yet another aspect of the present disclosure, transmitting, by way of the asynchronous network, the safety alert to the global safety monitor in the networked computing node includes transmitting by way of a respective path including at least one of (a) one or more of first communication paths of the asynchronous network or (b) one or more of second communication paths of the synchronous network, another one of the subunits, and the one or more of the first communication paths of the asynchronous network.

In still another aspect of the present disclosure, the action includes inhibiting motors of one or more of the plurality of subunits that are associated with the safety alert.

According to yet another aspect of the present disclosure, systems and methods are provided that address the above-mentioned needs. In an aspect of the present disclosure, a surgical robotic system is provided. The system includes a networked computing node, a slave robot assembly, a plurality of first communication paths, and a plurality of second communication paths. The slave robot assembly, including a plurality of subunits. The plurality of subunits are communicatively coupled to one another by way of the plurality of first communication paths, thereby forming at least a portion of a synchronous network. The networked computing node and at least one of the plurality of subunits are communicatively coupled to one another by way of one or more of the plurality of second communication paths, thereby forming at least a portion of an asynchronous network, and are configured to communicate one or more packets to one another by way of the asynchronous network. The at least one of the plurality of subunits is configured to communicate, with other ones of the plurality of subunits by way of the synchronous network, data from the one or more packets. A clock rate of the synchronous network is independent from a clock rate of the asynchronous network.

In another aspect of the present disclosure, the surgical robotic system further comprises a surgeon console, wherein the surgeon console, the networked computing node, and the at least one of the plurality of subunits are communicatively coupled to one another by way of one or more of the plurality of second communication paths, thereby forming at least another portion of the asynchronous network.

In yet another aspect of the present disclosure, the plurality of subunits are communicatively coupled to each other, by way of the plurality of first communication paths, in a ring topology.

In still another aspect of the present disclosure, the first subunit is further configured to receive a first packet, by way of the synchronous network, from a second subunit amongst the plurality of subunits. A priority level associated with data in the first packet is identified. A determination is made as to whether the priority level associated with the data exceeds a first threshold priority level. In response to determining whether the priority level associated with the data is above the first threshold priority level, the data in the first packet is transmitted to the networked computing node by way of the asynchronous network.

In another aspect of the present disclosure, a first subunit amongst the plurality of subunits further includes a memory that stores one or more local resolution rules. The first subunit amongst the plurality of subunits is further configured to determine whether the priority level associated with the data is below a second threshold priority level, and, in response to determining whether the priority level associated with the data is below the second threshold priority level: identify, based on the one or more local resolution rules, an action related to the data; generate a set of instructions based on the determined action; and transmit, by way of the synchronous network, a second packet comprising the set of instructions to the second subunit.

In a further aspect of the present disclosure, the first subunit amongst the plurality of subunits is further configured to, in response to determining whether the priority level associated with the data is below the first threshold priority level and above a second threshold priority level: determine, based on the one or more local resolution rules, whether an action related to the data can be performed by the second subunit. In response to determining whether the action relating to the data can be performed by the second subunit: a set of instructions is generated based on the action; and transmit, a second packet comprising the set of instructions is transmitted to the second subunit by way of the synchronous network.

In another aspect of the present disclosure, the first subunit amongst the plurality of subunits is further configured to, in response to determining whether the action relating to the data cannot be performed by the second subunit, transmit, by way of the asynchronous network, the data in the first packet to the networked computing node.

In yet another aspect of the present disclosure, the second subunit is coupled to an image capturing apparatus and the data is related to one or more images captured by the image capturing apparatus.

In still another aspect of the present disclosure, the priority level associated with the data is at least one of low priority, medium priority, or high priority.

In a further aspect of the present disclosure, the data is associated with a type of data and the one or more local resolution rules include one or more actions for each type of data.

In another aspect of the present disclosure, the type of data associated with the data is at least one of image data, positional data, intermediate calculation data, or error data.

In yet another aspect of the present disclosure, the one or more subunits of the slave robot assembly are configured to communicate with each other using Ethernet for Control Automation Technology (EtherCAT).

In still a further aspect of the present disclosure, the plurality of subunits are configured to communicate a packet with each other by way of one or more of the plurality of first communication paths, wherein a destination address field of the packet includes an identifier associated with one subunit of the plurality of subunits.

In another aspect of the present disclosure, the size of the destination address field is represented by a plurality of bit fields, and, for each of the plurality of subunits, an identifier associated with the respective one of the plurality of subunits is represented by a subset of the plurality of bit fields.

In yet another aspect of the present disclosure, the one or more packets have a fixed size.

In another aspect of the present disclosure, at least one of the plurality of subunits of the slave robot assembly is a robot arm unit.

In still another aspect of the present disclosure, at least one of the plurality of subunits of the slave robot assembly is an instrument drive unit.

In a further aspect of the present disclosure, at least one of the plurality of subunits of the slave robot assembly is a cart unit.

In yet another aspect of the present disclosure, the plurality of subunits of the slave robot assembly includes a cart unit, a setup arm unit, a robot arm unit, and an instrument drive unit.

In accordance with another aspect of the present disclosure, a method for allocating control among components of a slave robot assembly is provided. The method includes receiving, by a first subunit among a plurality of subunits of a slave robot assembly of a surgical robotic system, a first packet from a second subunit amongst a plurality of subunits, by way of a synchronous network comprising a plurality of first communication paths by which the plurality of subunits are communicatively coupled to one another. A priority level associated with data in the first packet is identified by the first subunit. The first subunit determines whether the priority level associated with the data exceeds a first threshold priority level. In response to determining whether the priority level associated with the data is above the first threshold priority level, the first subunit transmits the data in the first packet to a networked computing node by way of an asynchronous network comprising a plurality of second communication paths by which the networked computing node and at least one of the plurality of subunits are communicatively coupled to one another. A clock rate of the synchronous network is independent from a clock rate of the asynchronous network.

BRIEF DESCRIPTION OF THE DRAWINGS

Various aspects and features of the present disclosure are described herein below with references to the drawings, wherein.

DETAILED DESCRIPTION

Figure 1:
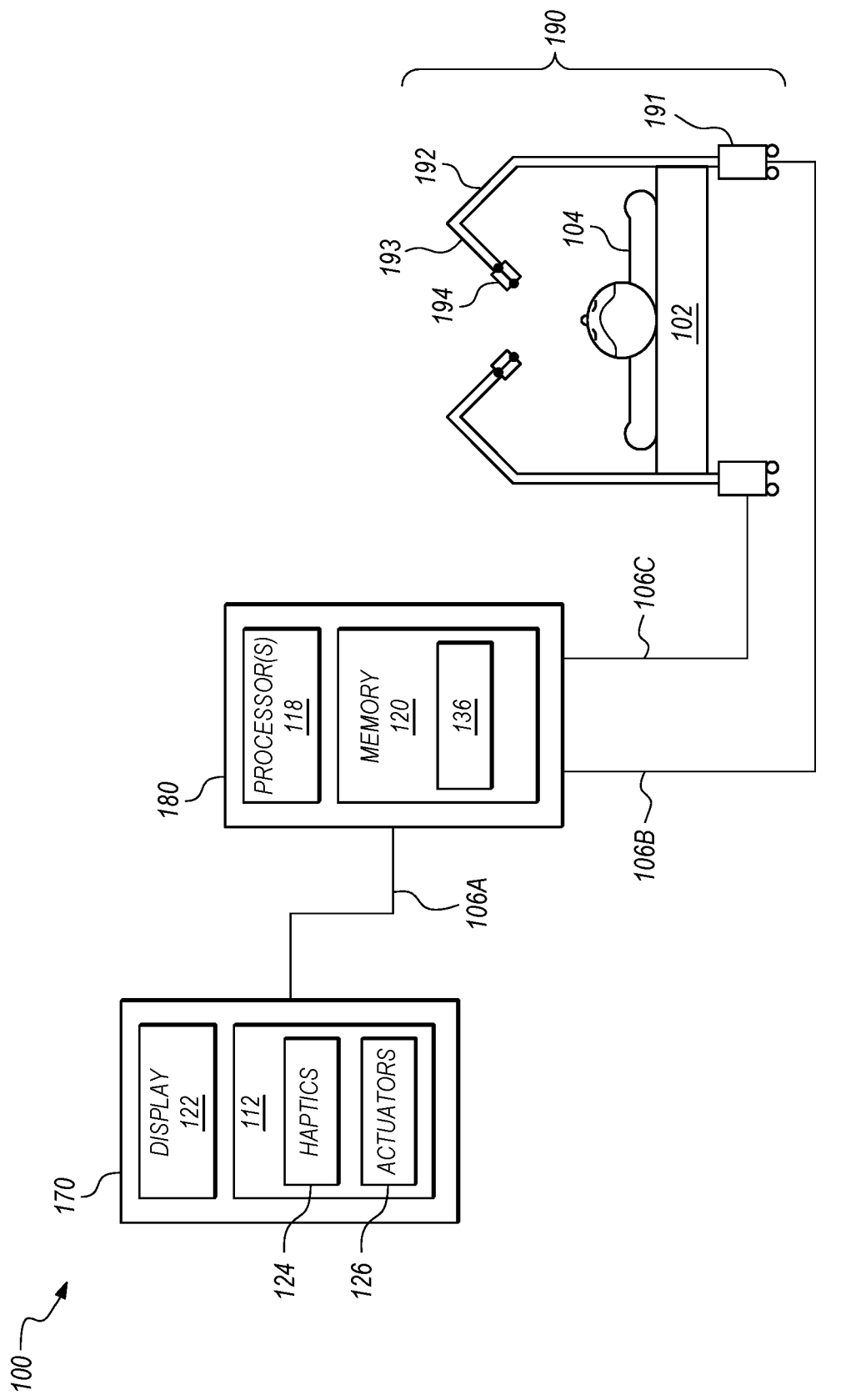
FIG. 1 illustrates an example robotic surgical system, in accordance with an exemplary embodiment herein.

The present disclosure is directed to surgical robotic systems including synchronous and asynchronous networks and communication methods employing the synchronous and asynchronous networks. In particular, the systems and methods described herein allow for designing and implementing a surgical robotic system that employs components in an asynchronous network and a synchronous network. The components are communicatively coupled to one another, and utilizing the asynchronous network, the synchronous network, and communication paths between them, the surgical robotic system makes decisions locally at the component level within the synchronous network first, and if a decision cannot be made locally at the component level within the synchronous network first, then the surgical robotic system makes the decision at a global or system level using a component within the asynchronous network. Utilizing the technologies, techniques, and embodiments described herein, overall latency of a surgical robotic system is reduced and operational and data communication efficiency of the surgical robotic system is improved.

Embodiments of the present disclosure are now described in detail with reference to the drawings in which like reference numerals designate identical or corresponding elements in each of the several views. As used herein, the term "clinician" refers to a doctor, a nurse, technician, medical assistant, or similar support personnel or any other person that may use the surgical robotic systems described herein. Throughout this description, the term "asynchronous network" refers to a network that is defined by a set of computing devices and one or more communication paths, configured so that the computing devices are communicatively coupled to one another by way of the one or more communication paths and are configured to communicate data and/or other information with one another by way of those communication paths in an asynchronous manner, for instance, without requiring clock signals in the transmitting and receiving computing devices to be synchronized. Throughout this description, the term "synchronous network" refers to a network that is defined by a set of computing devices and one or more communication paths, configured so that the computing devices are communicatively coupled to one another by way of the one or more communication paths and are configured to communicate data and/or other information with one another by way of those communication paths in a synchronous manner, for instance, by using clock signals in the transmitting and receiving computing devices that are synchronized with one another. Overlap may exist between the computing devices and/or the communication paths that define the asynchronous networks and the synchronous networks described herein. For example, a computing device and/or a communication path may be included as part of an asynchronous network and also be included as part of a synchronous network. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
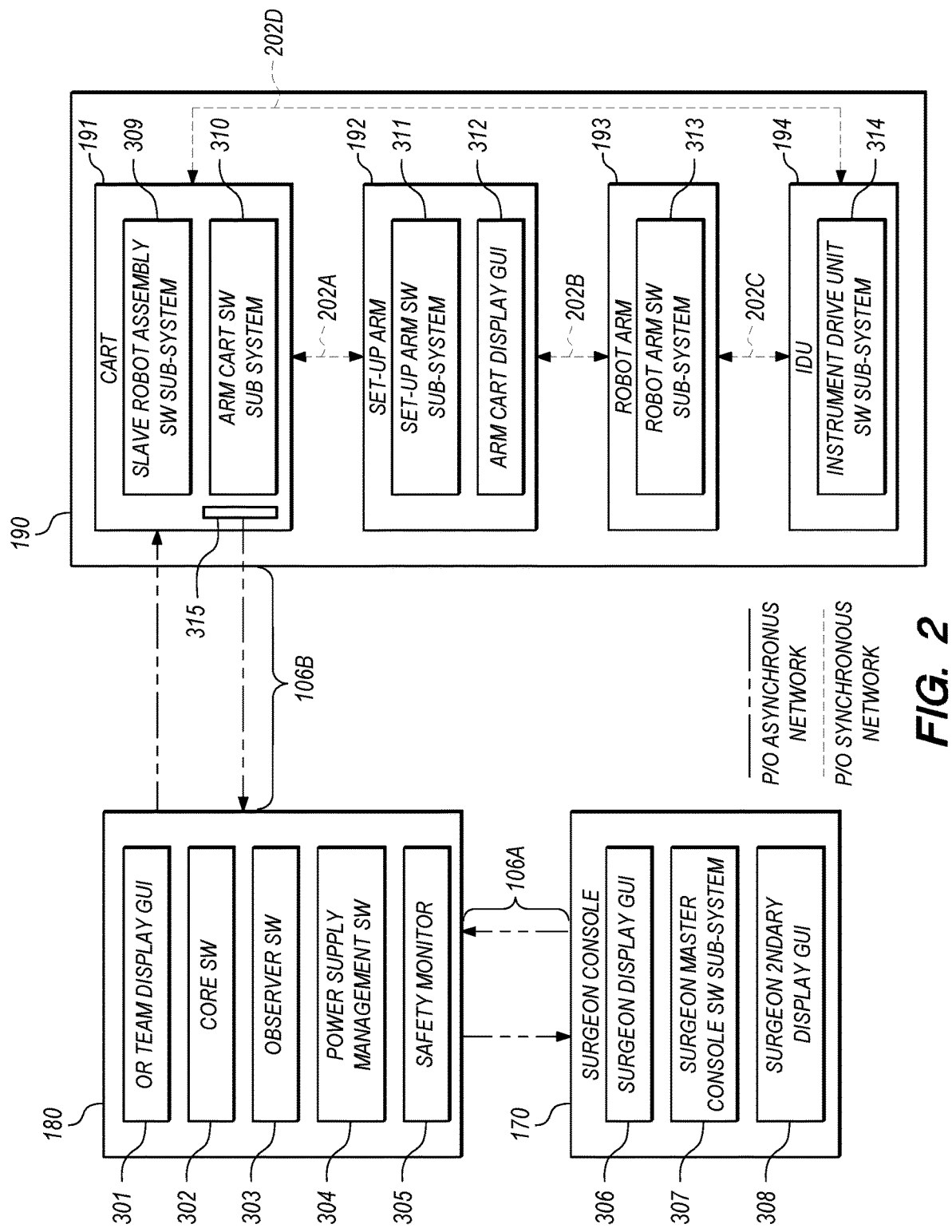
FIG. 2 is a schematic diagram illustrating an example embodiment by which various components of the robotic surgical system of FIG. 1 form an asynchronous network and a synchronous network, in accordance with an exemplary embodiment herein.

Referring now to FIG. 1, an example robotic surgical system 100 that is employed in accordance with various example embodiments herein is shown. The system 100 is an exemplary system employed in an operating room. The specific number of components of the system 100 depicted in FIG. 1 and the arrangement and configuration thereof are provided for illustrative purposes only, and should not be construed as limiting. For instance, various embodiments herein employ fewer or greater than all of the components shown in FIG. 1. For instance, additional components of the system 100 are shown in FIG. 2 and in FIG. 4. Additionally, the system 100 depicted in FIG. 1 is provided as an illustrative context in which various exemplary embodiments herein are applicable. However, the various exemplary embodiments herein are also applicable in contexts other than robotic surgical systems.

The system 100 includes an operating table 102 upon which a patient 104 lies during a surgical procedure, a surgeon console 170 with which a clinician, a user, or surgeon interacts during the surgical procedure, a networked computing node 180, and one or more slave robot assemblies 190. For convenience, the present description is made in the context of a single slave robot assembly 190, but it should be understood that the present disclosure is similarly applicable to embodiments that include multiple slave robot assemblies 190. The surgeon console 170, the networked computing node 180, and the slave robot assembly 190 are communicatively coupled to one another by way of respective communication paths 106 (individually, 106a, 106b, and 106c), which, in various embodiments herein, may be implemented as wired communication paths and/or as wireless communication paths. In particular, the surgeon console 170 and the networked computing node 180 are communicatively coupled to one another by way of the communication path 106a. The networked computing node 180 and the slave robot assembly 190 are communicatively coupled to one another by way of the communication path 106b. The surgeon console 170 and the slave robot assembly 190 are communicatively coupled to one another by way of the communication path 106a, the networked computing node 180, and the communication path 106b. As described in further detail below, in some embodiments, the surgeon console 170, the networked computing node 180, and the slave robot assembly 190, in conjunction with the communication paths 106, define an asynchronous network (not separately shown in FIG. 1) by which the surgeon console 170, the networked computing node 180, and the slave robot assembly 190 are configured to communicate data and/or other information with one another in an asynchronous manner. While described as an asynchronous network herein, those skilled in the art will appreciate that the network formed by the surgeon console 170, the networked computing node 180, and the slave robot assembly 190, in conjunction with the communication paths 106, may alternatively be a synchronous network. As also described in further detail below, the system 100 may be configured to implement a publish-subscribe messaging pattern to enable different components within the system 100 to communicate with each other. Additional details of the communication between the surgeon console 170, the networked computing node 180, and the slave robot assembly 190 are provided herein in the contexts of FIG. 2, FIG. 3, FIG. 4, and FIG. 5.

The slave robot assembly 190 includes multiple subunits 191, 192, 193, and 194, namely, a cart unit 191, a setup arm unit 192, a robot arm unit 193, and an instrument drive unit (IDU) 194. The subunits 191, 192, 193, and 194, of the slave robot assembly 190 are operably coupled to each other subunit 191, 192, 193, and 194 of the slave robot assembly 190 either directly or indirectly. For example, the cart unit 191 is operably coupled to the setup arm unit 192, the robot arm unit 193, and the instrument drive unit 194. Similarly, the setup arm unit 192 is operably coupled to the cart unit 191, the robot arm unit 193, and the instrument drive unit 194, while the robot arm unit 193 is operably coupled to the cart unit 191, the setup arm unit 192, the instrument drive unit 194, and the instrument drive unit 194 is operably coupled to the cart unit 191, the setup arm unit 192, and the robot arm unit 193. The subunits 191, 192, 193, and 194 are also communicatively coupled to each other subunit 191, 192, 193, and 194 of the slave robot assembly 190 either directly or indirectly by way of one or more communication paths (not shown in FIG. 1), thereby defining a synchronous network. The cart unit 191 is arranged adjacent to the operating table 102 within range of the patient 104 undergoing the surgical procedure. The instrument drive unit 194 is couplable to one or more corresponding surgical instruments (not shown in FIG. 1) that may be interchangeably fastened thereto. The cart unit 191 is configured to move along side of the operating table 102 or the patient 104. The cart unit 191 is configured to move towards and away from the patient 104.

The networked computing node 180 is a computing device that includes one or more processors 118 and one or more memory units 120. The networked computing node 180 may further include one or more communications interfaces, such as network interfaces to facilitate communication with the surgeon console 170, the slave robot assembly 190, and/or external devices via a network and/or the Internet. In various embodiments, the networked computing node 180 may be integrated with the surgeon console 170, or may be a standalone device, such as a computing tower, disposed within or near the operating room. The memory unit 120 stores instructions 136 (in an example, software) that the processor 118 executes to perform procedures of the various embodiments herein. As will be appreciated, the processor 118 and the memory units 120 implementation is provided by way of example only, and should not be construed as limiting. For instance, procedures of any of the embodiments of the present disclosure may be implemented by hardware components, firmware components, software components, and/or any combination thereof. Additional details of networked computing node 180 are provided below in the contexts of FIG. 2, FIG. 3, FIG. 4, and FIG. 5.

The surgeon console 170 includes a display device 122 and handles 112 with which the surgeon interacts during a surgical procedure. The handles 112, in some embodiments, include various haptics 124 and/or actuators 126. During operation of the surgical system 100, the surgeon moves the handles 112 of the surgeon console 170 to produce a corresponding movement and/or actuation of the setup arm unit 192, the robot arm unit 193, the instrument drive unit 194, and/or one or more surgical instruments (not shown in FIG. 1) coupled to the instrument drive unit 194. Based on the surgeon's input command, the handles 112 provide, by way of the communication path 106*a*, a signal to the networked computing node 180, which then provides, by way of the communication path 106*b*, a corresponding signal to the cart unit 191 of the slave robot assembly 190, which provides, by way of other communication paths (not shown in FIG. 1), corresponding signals or instructions to the setup arm unit 192, the robot arm unit 193, the instrument drive unit 194 in order to cause the performance of commanded action. In some embodiments, the slave robot assembly 190 includes one or more drive motors (not shown in FIG. 1), which are coupled to the setup arm unit 192, the robot arm unit 193, and/or the instrument drive unit 194, in order to cause motion of the corresponding subunit 192, 193, 194 and/or of the surgical instrument (not shown in FIG. 1) coupled thereto.

In some embodiments, the various haptics 124 in the handles 112 provide feedback to the surgeon relating to various tissue parameters or conditions, in an example, tissue resistance due to manipulation, cutting, or otherwise treating, pressure by the instrument onto the tissue, tissue temperature, tissue impedance, etc. As can be appreciated, such haptics 124 provide the surgeon with enhanced tactile feedback simulating actual operating conditions. The haptics 124 may include vibratory motors, electroactive polymers, piezoelectric devices, electrostatic devices, subsonic audio wave surface actuation devices, reverse-electrovibration, or any other device capable of providing a tactile feedback to a user. As mentioned above, the handles 112 may also include a variety of different actuators 126, which, for instance, may be employed for delicate tissue manipulation and/or treatment further enhancing the surgeon's ability to mimic actual operating conditions.

As mentioned above, one or more surgical instruments (not separately shown in FIG. 1) may be interchangeably fastened to the instrument drive unit 194, depending on the particular surgical procedure being performed. Although any type of surgical instrument may be employed, example types of such surgical instruments include, by way of example and not limitation, an image capture device, a probe, an end effector, a grasper, a knife, scissors, and/or the like. In accordance with some embodiments herein, one or more of the surgical instruments coupled to the instrument drive unit 194 is a probe (not shown in FIG. 1), which includes a stereoscopic image capture device, and is inserted into the patient 104 in order to capture images of a region of interest inside the patient 104 during a surgical procedure. The images captured by the image capture device are communicated to the display device 122 (also referred to herein as a "display") of the surgeon console 170 that displays the images to the surgeon.

FIG. 2 shows a block diagram that depicts additional aspects of the surgical system 100, including additional components of the surgeon console 170, the networked computing node 180, and the slave robot assembly 190. Also shown in FIG. 2 are exemplary topologies of the asynchronous network defined at least in part by communication paths 106*a* and 106*b* and the synchronous network defined at least in part by communication paths 202*a*, 202*b*, 202*c*, and 202*d* (collectively, 202). By virtue of the configuration and functionality of the surgeon console 170, the networked computing node 180, the slave robot assembly 190, and the communication paths 106 and 202, which define the asynchronous and synchronous networks, respectively, the individual components of the surgical robotic system 100 are enabled to operate and/or communicate in an efficient manner, for instance, that mitigates various types of latency, such as latency between a surgeon inputting a movement command by way of the surgeon console 170 and the actual movement of the corresponding subunit 191, 192, 194, and 194. For example, in various embodiments, the subunits 191, 192, 194, and 194 of the slave robot assembly 190 are configured to communicate with one another, independently from the surgeon console 170 and/or the networked computing node 180, by way of the synchronous network that is defined at least in part by the communication paths 202. Concurrently, the surgeon console 170, the networked computing node 180, and/or the slave robot assembly 190 are configured to communicate with one another by way of the asynchronous network that is defined at least in part by the communication paths 106. By allocating components of the system 100 to parallel asynchronous and synchronous networks and allocating functionality (such as power management functionality) to particular components of the system 100, efficiency of operational performance, communication, and/or the like is improved. For example, when circumstances arise under which one or more of the subunits 191, 192, 194, and 194 of the slave robot assembly 190 requires processing, communication, and/or the like from the surgeon console 170 and/or the networked computing node 180, the subunits 191, 192, 194, and 194 are configured to communicate with the surgeon console 170 and/or the networked computing node 180. However, the subunits 191, 192, 194, and 194 of the slave robot assembly 190 are configured to handle certain processing, communication, and/or other computing tasks without requiring processing, communication, and/or the like from the surgeon console 170 and/or the networked computing node 180, thereby freeing up the processing and/or communication bandwidth of the surgeon console 170 and/or the networked computing node 180. This enables the surgeon console 170 and/or the networked computing node 180 to accommodate a greater number of slave robot assemblies 190, thereby increasing the capabilities and flexibility of the surgical robotic system 100.

Communication between the surgeon console 170, the networked computing node 180, and the slave robot assembly 190 includes real-time communication and non-real-time communication. As used herein, the term "real-time communication" refers to transmission of data (for example, data relating to errors in the surgical system 100, alerts about significant risks to the surgical system 100, other critical data, etc.) corresponding to events as they occur. As used herein, the term "non-real-time communication" refers to transmission of data (for example, non-critical data) corresponding at times when the networked computing node 180 is not heavily used or at off-peak hours.

As shown in FIG. 2, the surgeon console 170 includes a surgeon display graphical user interface (GUI) 306, a surgeon master console software subsystem 307, and a surgeon secondary display GUI 308. Although not separately shown in FIG. 2, the surgeon console 170, in some embodiments, includes one or more processors coupled to one or more memory units storing instructions that, when executed by the one or more processors, cause the surgeon console 170 to implement the surgeon display graphical user interface (GUI) 306, the surgeon master console software subsystem 307, and/or the surgeon secondary display GUI 308. In this manner, for example, the surgeon console 170 is configured to execute procedures, such as programs, scripts, or other executable commands, that enable a user, such as a surgeon, to interact with one or more setup arm units 192, robot arm units 193, and/or instrument drive units 194 via the networked computing node 180 and the slave robot assembly 190. The surgeon console 170 is further configured to generate the surgeon display GUI 306 to present information to the surgeon by way of the display unit 122.

In some embodiments, the display unit 122 of the surgeon console 170 is a touchscreen able to receive touch input from the surgeon. The display unit 122 of the surgeon console 170 is configured to identify and determine pressure and length of touch. In some embodiments, the surgeon display GUI 306 is configured to determine the length of the time of the touch input and, based on the length of the time of the touch input, the surgeon display GUI 306 may present one or more different graphical user interface items. For example, if the surgeon display GUI 306 is displaying a "back" button, simply touching the "back" button may result in the screen going back to the previous screen of the surgeon display GUI 306, and if the surgeon pushes and holds down the back button for a certain amount of time, then a menu may drop down providing one or more surgeon console operation options to the surgeon.

Although not shown in FIG. 1, the surgeon console 170, in some embodiments, includes a second display unit, in which case the surgeon console 170 is further configured to generate the surgeon secondary display GUI 308 to present information to the surgeon by way of the secondary display unit in a manner similar to that described above in connection with the surgeon display GUI 306.

The surgeon master console software subsystem 307 is operatively coupled to the surgeon display GUI 306 and the surgeon secondary display GUI 308 and is generally configured to perform the functions of the surgeon console 170. For example, the surgeon master console software subsystem 307 is configured to capture, record, and/or analyze inputs from the surgeon, and/or communicate data to and from the networked computing node 180 and/or the slave robot assembly 190. In some embodiments, the surgeon master console software subsystem 307 is coupled to an operating system (not shown in FIG. 2) of the surgeon console 170 and/or to one or more other components of the surgeon console 170, such as one or more applications that implement internetworking functions. Examples of such internetworking functions include, without limitation, one or more packet communication or transmission protocols, including machine-to-machine communication protocols, such as a Data Distribution Service protocol for Real-Time Systems (DDS) including Real-Time Publish Subscribe Protocol (RTPS). The packet transmission protocols implemented by the internetworking functions enable scalable, real-time, dependable, high performance, interoperable packet or data exchanges between publishers and subscribers of system 100. As described herein, "publishers" are senders of a message or data and "subscribers" are receivers of a message or data. As described above, the surgical robotic system 100, in some examples, implements a publish-subscribe messaging pattern whereby publishers may transmit messages to subscribers by classifying messages into classes. Subscribers may indicate interest in particular classes and receive messages associated with or classified into the particular classes.

Each class is associated with a particular identifier and a publisher may classify messages into particular classes by associating the messages with the identifier of the classes. Subscribers are associated with certain identifiers of classes and receive messages that are associated with the identifiers. In some embodiments, the internetworking functions of ingress interfaces of the subscriber are configured to determine the class identifiers associated with the subscriber and receive messages associated with those class identifiers. The messages may be encapsulated within a packet based on the communication or transmission protocols being used. In some embodiments, certain fields or bits of a packet may comprise the identifier of the class associated with the message. The ingress interfaces of the subscriber may be configured to determine the identifier of the class associated with the message by reading the fields or bits of the packet.

A computing node may be both a publisher of a message and a subscriber of another message. For example, the surgeon console 170 may be a publisher of a message that the surgeon console 170 sends or transmits to the networked computing node 180 and the surgeon console 170 may be a subscriber of a message that the surgeon console 170 receives from networked computing node 180. In some embodiments, the surgeon console 170 may be a publisher of a message that the surgeon console 170 sends or transmits to the slave robot assembly 190 and the surgeon console 170 may be subscriber of a message that the surgeon console 170 receives from the slave robot assembly 190.

With continued reference to FIG. 2, the networked computing node 180 includes an operating room (OR) team display GUI 301, core software 302, observer software 303, power supply management software 304, and a global safety monitor 305. Although not separately shown in FIG. 2, the networked computing node 180, in some embodiments, includes one or more processors 118 coupled to one or more memory units 120 storing instructions that, when executed by the one or more processors, cause the networked computing node to implement the operating room team display GUI 301, core software 302, observer software 303, power supply management software 304, and/or global safety monitor 305. In this manner, for example, the networked computing node 180 is configured to execute procedures, such as programs, scripts, or other executable commands, that enable a user, such as a surgeon, to effectuate operation of one or more setup arm units 192, robot arm units 193, and/or instrument drive units 194 of the slave robot assembly 190 by way of the surgeon console 170. In some instances, the networked computing node 180 operates as an interface between the surgeon console 170 and the slave robot assembly 190 that translates or otherwise processes information received from one of the surgeon console 170 and the slave robot assembly 190 and communicates the information to the other of the surgeon console 170 and the slave robot assembly 190, respectively.

Although not shown in FIG. 1 or FIG. 2, in some embodiments, the networked computing node 180 includes, or is coupled to, a display unit configured to display information, such as one or more images, or a stream of images, to OR personnel. The display unit may be configured such that visibility of information or images displayed on the display unit may be easily visible by anyone in the OR. In such embodiments, the networked computing node 180 is configured to generate the OR team display GUI 301 to present information to the OR personnel by way of the display unit of the networked computing node 180.

The operating room team display GUI 301 is operatively coupled to the core software system 302 such that inputs from users or clinicians are captured, recorded and analyzed by the core software system 302 and other systems coupled to the core software system 302. In various embodiments, the core software system 302 is coupled to an operating system (not separately shown in FIG. 2) of the networked computing node 180 and/or to one or more other applications of the networked computing node 180, such as applications that implement internetworking functions.

The core software system 302 is also operatively coupled to the observer software system 303, which is an industrial controls system that includes protocols and tools configured to observe and control other components of the system 100, such as the slave robot assembly 190. For instance, the observer software system 303 is configured to observe various operational states of components of the system 100 that are operatively coupled with the networked computing node 180. For example, the observer software system 303 may observe various operational states of the slave robot assembly 190, including power on and power off states. The observer software system 303 is also configured to transmit information associated with various operational states of the components of the system 100 to the core software system 302. In some embodiments, the core software system 302 is configured to determine, based on the operational state of a component of the system 100, one or more instructions to be executed and/or actions to be performed.

The core software system 302 is also operatively coupled to the power supply management software system 304, which is configured to determine power usage by various components of the system 100, such as power usage of the slave robot assembly 190 and various components of the slave robot assembly 190, such as the cart unit 194, the setup arm unit 192, the robot arm unit 193, and/or the instrument drive unit 194. The power supply management software system 304 is configured to store various power usage metrics, rules, and/or thresholds and determine, based on a set of power usage rules associated with power usage by various components of the system 100, one or more instructions to be executed and/or actions to be performed. The core software system 302 is, in some examples, configured to forward requests for changes in power supplied to or used by a component of the system 100 to the power supply management software system 304 to ensure compliance with the power usage rules.

The power supply management software system 304 is configured to determine whether the requested change is allowed or feasible based on power usage metrics and/or rules associated with power usage. For example, if the networked computing node 180 receives, from the surgeon console 170 by way of one of the communication paths 106a, a request to increase power used to drive a surgical instrument coupled to the instrument drive unit 194, the core software system 302 forwards the request to increase power to the power supply management software system 304. The power supply management software system 304 determines, based on the rules associated with power usage of the instrument drive unit 194, that the power currently used in driving the surgical instrument coupled to the instrument drive unit 194 is below the maximum power with which the instrument of the instrument drive unit 194 is permitted to be driven and, in response, forwards to the IDU software subsystem 314 by way of one or more of the communication paths 106 and 202, an instruction to increase power used in driving the surgical instrument coupled to the instrument drive unit 194. In some embodiments, the power supply management software system 304 forwards the instruction to the core software system 302 and the core software system 302 transmits the instructions to the slave robot assembly 190.

The core software system 302 also is operatively coupled to the global safety monitor system 305. The global safety monitor system 305 includes one or more rules to determine whether various safety thresholds of the system 100 are exceeded. The global safety monitor system 305 monitors safety levels of each component of the system 100, including the networked computing node 180, the surgeon console 170, and the slave robot assembly 190 and components thereof. A safety level of a system is determined by comparing one or more safety metrics (for example, determined by sensors or other measurement devices, not separately shown in FIG. 1 or FIG. 2) of a component and then determining whether those metrics are within configured safety thresholds by comparing the metrics with the one or more rules of the global safety monitor 305. Additional details of the global safety monitor system 305 are provided below in the context of FIG. 4.

As described above, the system 100 also includes one or more slave robot assemblies, such as the slave robot assembly 190, and each slave robot assembly may include a cart unit, a setup arm unit, a robot arm unit, an instrument drive unit, such as the cart unit 191, the setup arm unit 192, the robot arm unit 193, the instrument drive unit 194, respectively. In general, the cart unit 191, setup arm unit 192, robot arm unit 193, and instrument drive unit 194 of the slave robot assembly 190, together with the communication paths 202, define a synchronous network, in which the clocks used by each of the subunits 191, 192, 193, and 194 are synchronized to one another. The topology of the synchronous network of the slave robot assembly 190 may be any network topology that allows for an efficient synchronous network, such as a ring network topology, including a unidirectional ring network, a bidirectional ring network, and/or the like. The various components of the slave robot assembly 190, such as the cart unit 191, the setup arm unit 192, the robot arm unit 193, the instrument drive unit 194 are configured to utilize one or more communication protocols, such as Ethernet for Control Automation Technology (EtherCAT), to communicate with each other by way of the communication paths 202.

As shown in FIG. 2, the cart unit 191 includes a slave robot assembly software subsystem 309, an arm cart software subsystem 310, and a data controller 315. Although not separately shown in FIG. 2, the cart unit 191, in some embodiments, includes one or more processors coupled to one or more memory units storing instructions that, when executed by the one or more processors, cause the cart unit 191 to implement the slave robot assembly software subsystem 309 and the arm cart software subsystem 310. In this manner, for example, the cart unit 191 is configured to execute certain procedures, such as programs, scripts, or other executable commands, that enable a user, such as a surgeon, to move the cart unit 191 along the side of the operating table, among other operations. The cart unit 191, in some examples, is configured to receive one or more packets from other components of the system 100, such as the networked computing node 180, and/or the surgeon console 170.

In some embodiments, the slave robot assembly software sub-system 309 is coupled to one or more other applications of the slave robot assembly 190, such as an application that implements internetworking functions, including one or more packet communication or transmission protocols, such as EtherCAT. The slave robot assembly software subsystem 309 includes one or more sets of rules that the slave robot assembly software subsystem 309 utilizes to determine an instruction to be executed and/or an action to be performed, based on information associated with the various subunits 191, 192, 193, and 194 of the slave robot assembly 190. The slave robot assembly unit 190 is configured to make decisions using information associated with the cart unit 191, the setup arm unit 192, the robot arm unit 193, the instrument drive unit 194. Additional details of analyzing and determining instructions based on information associated with the various units of the slave robot assembly 190 are provided below in the context of FIG. 4, FIG. 5, and FIG. 6.

The slave robot assembly software subsystem 309 is configured to receive, in an asynchronous manner, one or more packets from other components of the system 100, such as the networked computing node 180 and the surgeon console 170, by way one or more of the communication paths 106a and 106b. To promote efficient communication, in some embodiments, packets received by the slave robot assembly 190 are of a fixed size and certain bits of data within the packet are associated with certain components of the slave robot assembly 190. The slave robot assembly software subsystem 309 is configured to identify the component of the slave robot assembly 190 that is associated with the certain bits of data within the packet and, where appropriate, forward the data carried by the bits to the appropriate component of the slave robot assembly 190 in a synchronous manner by way of one or more of the communication paths 202. For example, packets communicated to the slave robot assembly software subsystem 309 may be configured such that the first 128 bits of a packet are associated with the cart unit 191, the next 128 bits of the packet are associated with the setup arm unit 192, the next 128 bits of the packet are associated with the robot arm unit 193, and the next 128 bits of the packet are associated with the instrument drive unit 194. The packets may also include respective flags that correspond to the subunits 191, 192, 193, and 194 and that, depending on their value, indicate whether the packet includes data for the respective subunits 191, 192, 193, and 194. The slave robot assembly software subsystem 309 is configured to identify the intended destination of the packet based on the values of the flags and/or the bits that are present in the packet. If the packet includes data intended for the cart unit 191 itself, the slave robot assembly software subsystem 309, which is operably coupled to the cart software subsystem 310 forwards the data to the cart software subsystem 310, which is configured to determine, based on the data, an instruction to be executed by the cart unit 191.

The slave robot assembly software subsystem 309 is communicatively coupled to the data controller 315. For each packet received by the slave robot assembly software subsystem 309 from one of the other subunits of the slave robot assembly 190, the data controller 315 determines whether an action in response to the received data can be performed locally by the slave robot assembly 190 or whether the data should be transmitted to the networked computing node 180. Data transmitted to the slave robot assembly software subsystem 309 is associated with a type or category, referred to herein as data type. Each subunit of the slave robot assembly 190 is configured to associate data with various data types and a data type is added or removed from the slave robot assembly 190 through configuration data or modifications to the configuration data. Data types include, but are not limited to, image data, positional data, intermediate calculation data, error data.

Each data type is associated with a unique identifier and a subunit of the slave robot assembly 190, when transmitting data to the slave robot assembly software subsystem 309, is configured to include the unique identifier within the packet comprising the data that is being transmitted. In some embodiments, if data is transmitted in a series of packets, then each of the packets within the series of packets includes the unique identifier of the data type associated with the data. In some embodiments, if data is transmitted in a series of packets, then only the first packet within the series includes the unique identifier of the data type associated with the data, the last packet within the series includes a sequence of bits that indicates that all of the data has been transmitted, and the slave robot assembly software subsystem 309 is configured to associate the data type included in the first packet with data in the first packet, the last packet, and all intermediate packets.

Each data type is associated with a priority level and the slave robot assembly 190 includes a set of local action rules that indicate whether an action can be performed based on the priority level associated with the data type. In some embodiments, the priority levels are high priority, medium priority, low priority. The one or more local action rules specify at least one priority level for each data type that the subunits of the slave robot assembly 190 are configured to utilize. As described above, data types include, but are not limited to, image data, positional data, intermediate calculation data, error data, and in some embodiments, image data is associated with a high priority, intermediate calculation is associated with low priority, positional data is associated with medium priority, and error data is associated with medium priority.

For each priority level, one or more local action rules specify whether or not an action can be performed locally. For certain priority levels, the local action rules specify whether or not an action can be performed locally, based on the priority level and the data type associated with the received data. If an action cannot be performed locally, the local action rules specify that the data should be transmitted to the networked computing node 180. If an action can be performed locally, the local resolution rules specify machine readable instructions to perform the action. As described herein, the term "machine readable instructions" includes instructions and/or commands in the syntax of a programming language, or in binary code, etc. that the executing computing node is configured to process or execute. Examples of actions that the local action rules specify include, but are not limited to, calculating new positional data for subunit of the slave robot assembly 190, such as set-up arm unit 192, robot arm unit 193, and/or the like; transmitting image data from images captured by an image capturing device operably coupled to the slave robot assembly 190 to another computing node of system 100, such as the networked computing node 180, and/or the like; calculating and/or setting power levels of subunits of the slave robot assembly 190, such as set-up arm unit 192, robot arm unit 193, instrument drive unit 194, and/or the like; determining whether temperatures of the subunits of the slave robot assembly 190 are above a threshold temperature; calculating slack in cables of certain instruments, such as end-effectors, and/or the like that are coupled to the instrument drive unit 194; inhibiting power provision (such as by powering down) to one or more subunits of the slave robot assembly 190; and inhibiting a motor (such as by engaging brakes and/or inhibiting power provision) associated with one or more subunits of the slave robot assembly 190.

The data controller 315 is configured to identify the data type of data received by the slave robot assembly software sub-system 309, and, based on one or more local action rules and the data type, identify the priority level of the received data. The data controller 315 is configured to identify an action to perform, based on the priority level and one or more local action rules. If the data controller 315 identifies that the action cannot be performed locally, the data controller 315 transmits the data received by the slave robot assembly software sub-system 309 to the networked computing node 180. If the data controller 315 identifies that the action can be performed locally, then the data controller 315 performs the action and generates a set of instructions for the subunit that transmitted the data to the slave robot assembly software sub-system 309 to implement the performed action.

As described above, certain data types, such as positional data and error data, are associated with medium priority, and in response to the slave robot assembly software sub-system 309 receiving data associated with medium priority, the data controller 315 determines whether an action can be performed locally based on the priority level, the data type, and the local action rules. For example, in a case where the local action rules specify that actions for medium priority data and data type of positional data can be performed locally, while actions for data type of error data cannot be performed locally, then the data controller 315, in response to the slave robot assembly software sub-system 309 receiving positional data, calculates new positional data based on the specified machine readable instructions and, in response to slave robot assembly software sub-system 309 receiving error data, transmits the error data to the networked computing node 180.

The setup arm unit 192 includes a setup arm software sub-system 311 and an arm cart display GUI 312. Additionally, although not separately shown in FIG. 2, the setup arm unit 192, in some embodiments, includes one or more processors coupled to one or more memory units storing instructions that, when executed by the one or more processors, cause the setup arm unit 192 to implement the setup arm software subsystem 311 and the arm cart display GUI 312. In this manner, for example, the setup arm unit 192 is configured to execute certain procedures, such as programs, scripts, or other executable commands, that enable a user, such as a surgeon, to move the setup arm unit 192, among other operations.

Also, although not shown in FIG. 2, the setup arm unit 192 may be coupled to an arm cart display device and may be configured to display information by way of the display device. The information displayed on the display device may include, for instance, information associated with the position of the slave robot assembly 190, including the position of the cart unit 191 relative to the operating table, the position of the setup arm unit 192 relative to the patient and the operating table, the position of the robot arm unit 193, and/or the position of the instrument drive unit 194. The arm display GUI 312 may be operatively coupled to the setup arm software subsystem 311 such that inputs from users or clinicians are captured, recorded, and analyzed by the arm display GUI 312 and the inputs are transmitted to the setup arm software subsystem 311. The setup arm software subsystem 311 is configured to determine, based on information received in packets received by the slave robot assembly 190 and/or packets received from the cart unit 191, the robot arm unit 193, or the instrument drive unit 193, an instruction to be executed and/or an action to be performed by the setup arm unit 191. The setup arm software subsystem 311, in some embodiments, is configured to determine an instruction to be executed by one or more other components of the slave robot assembly 190 and to transmit the instructions and/or other data to the one or more other components of the slave robot assembly 190.

The robot arm unit 193 includes a robot arm software subsystem 313. Additionally, although not shown in FIG. 2, the robot arm unit 193, in some embodiments, also includes one or more processors coupled to one or more memory units storing instructions that, when executed by the one or more processors, cause the robot arm unit 193 to implement the robot arm software subsystem 313. In this manner, for example, the robot arm unit 193 is configured to execute certain procedures, such as programs, scripts, or other executable commands, that allow a user, such as a surgeon, among other operations, to move the robot arm unit 193 relative to the patient 104. The robot arm software subsystem 313 is, in some embodiments, coupled to one or more other applications of the slave robot assembly 190, and is configured to determine, based on packets received by the slave robot assembly 190 and/or packets received from the cart unit 191, the setup arm unit 192, or the instrument drive unit 193, an instruction to be executed and/or an action to be performed by the robot arm unit 193.

For example, the slave robot assembly 190 may receive configuration data associated with the robot arm unit 193 and the robot software subsystem 313 updates the configuration data of the robot arm unit 193 once the configuration data is received by the robot arm unit 193. The slave robot assembly 190 also receives operational mode data or instructions indicating operations for the robot arm unit 193 to perform, such as moving the robotic arm to a new position or suspending all operations of the robotic arm. The robot software sub-system 313 is configured to determine whether instructions for the robot arm unit 193 are valid and, if valid, cause the robot arm unit 193 to perform the operations. In some embodiments, the slave robot assembly software sub-system 309 is configured to determine whether any instruction for the slave robot assembly 190 is valid and if valid, transmit the instructions by way of the ring topology defined by the communication paths 202; and if the instructions were intended for the robot arm unit 193, then the robot software subsystem 313 causes the robot arm unit 193 to perform the operations associated with the instructions or commands without checking whether the instructions are valid.

The robot arm unit 193 transmits one or more packets to the networked computing node 180 or the surgeon console 170 by way of one or more of the communication paths 202, one or more of the other subunits 191, 192, and 194, and one or more of the communication paths 106. In this manner, the robot arm unit 193 transmits one or more packets to the networked computing node 180 or the surgeon console 170 by employing elements of both the synchronous network and the asynchronous network. The robot arm unit 193 transmits, among other data, data from any sensors coupled with the robotic arm of the robot arm unit 193 or any sensors coupled with the robot arm unit 193, position data of the robotic arm relative to the patient and/or the operating table, operational state or operational mode of the robot arm unit 193, current configuration data of the robot arm unit 193, and/or the like. The robot arm unit 193, in some examples, is configured to transmit the information to the arm cart unit 191 using EtherCAT and the arm cart unit 191 is configured to forward the data to the networked computing node 180.

The instrument drive unit 194 includes an instrument drive unit software subsystem 314. Additionally, although not shown in FIG. 2, the instrument drive unit 194, in some embodiments, includes one or more processors coupled to one or more memory units storing instructions that, when executed by the one or more processors, cause the instrument drive unit 194 to implement the instrument drive unit software subsystem 314. In this manner, for example, the instrument drive unit 194 is configured to execute certain procedures, such as programs, scripts, or other executable commands, that enable a user, such as a surgeon, to operate the surgical instrument coupled to the instrument drive unit 194 during a medical procedure, among other operations. The instrument drive unit software subsystem 314 is configured to determine, based on data received by the instrument drive unit 194, one or more actions to be performed by the instrument drive unit 194 and/or by the surgical instrument coupled thereto. The instrument drive unit software subsystem 314 is also configured to cause the instrument drive unit 194 and/or the surgical instrument to perform the determined one or more actions.

The instrument drive unit software sub-system 314 is configured to transmit one or more packets of data to the networked computing node 180 and/or to the surgeon console 170. In some embodiments, in order to transmit data to the networked computing node 180 or the surgeon console 170, the instrument drive unit software subsystem 314 transmits the data to the arm cart unit 191 in a synchronous manner by way of one or more of the communication paths 202, and the arm cart unit 191 forwards the data to the networked computing node 180. The networked computing node 180 then determines whether instructions or signals should be transmitted to the surgeon console 170 based on data received from the arm cart unit 191. The instrument drive unit 194 may transmit packets including, among other data, data captured or recorded by one or more sensors (not shown in FIG. 2) that are included or affixed to the surgical instrument coupled to the instrument drive unit 194. The instrument drive unit 194 transmits packets of data related to or associated with a position of the surgical instrument of the instrument drive unit 194, configuration data of the instrument drive unit 194, and/or the like. The instrument drive unit 194 also transmits, in some examples, operational mode data of the surgical instrument of the instrument drive unit 194.

In some embodiments, the instrument drive unit 194 receives one or more packets of configuration data and the instrument drive unit software subsystem 314 is configured to update configuration data of the instrument drive unit 194 based on the received configuration data. The instrument drive unit 194 also receives packets of operational mode data, such as a certain operating mode from among a number of operating modes, for the surgical instrument of the instrument drive 194 to enter. The instrument drive unit 194 also receives packets including commands for the surgical instrument, such as a command to start a certain operation of the surgical instrument or stop a certain operation of the surgical instrument, or to temporarily suspend any operations of the surgical instrument of the instrument drive unit 194.

In some embodiments, the subunits 191, 192, 193, and 194 of the slave robot assembly 190 are coupled to each other such that each of the subunits 191, 192, 193, and 194 is coupled to at least two other of the subunits 191, 192, 193, and 194 to form a ring topology. For example, in FIG. 2, the cart unit 191 is coupled to the setup arm unit 192 and the instrument drive unit 194. Similarly, the setup arm unit 192 is coupled to the cart unit 191 and the robot arm unit 193, and the robot arm unit 193 is coupled to the setup arm unit 192 and the instrument drive unit 194, and the instrument drive unit 194 is coupled to the robot arm unit 193 and the cart unit 191.

Figure 3:
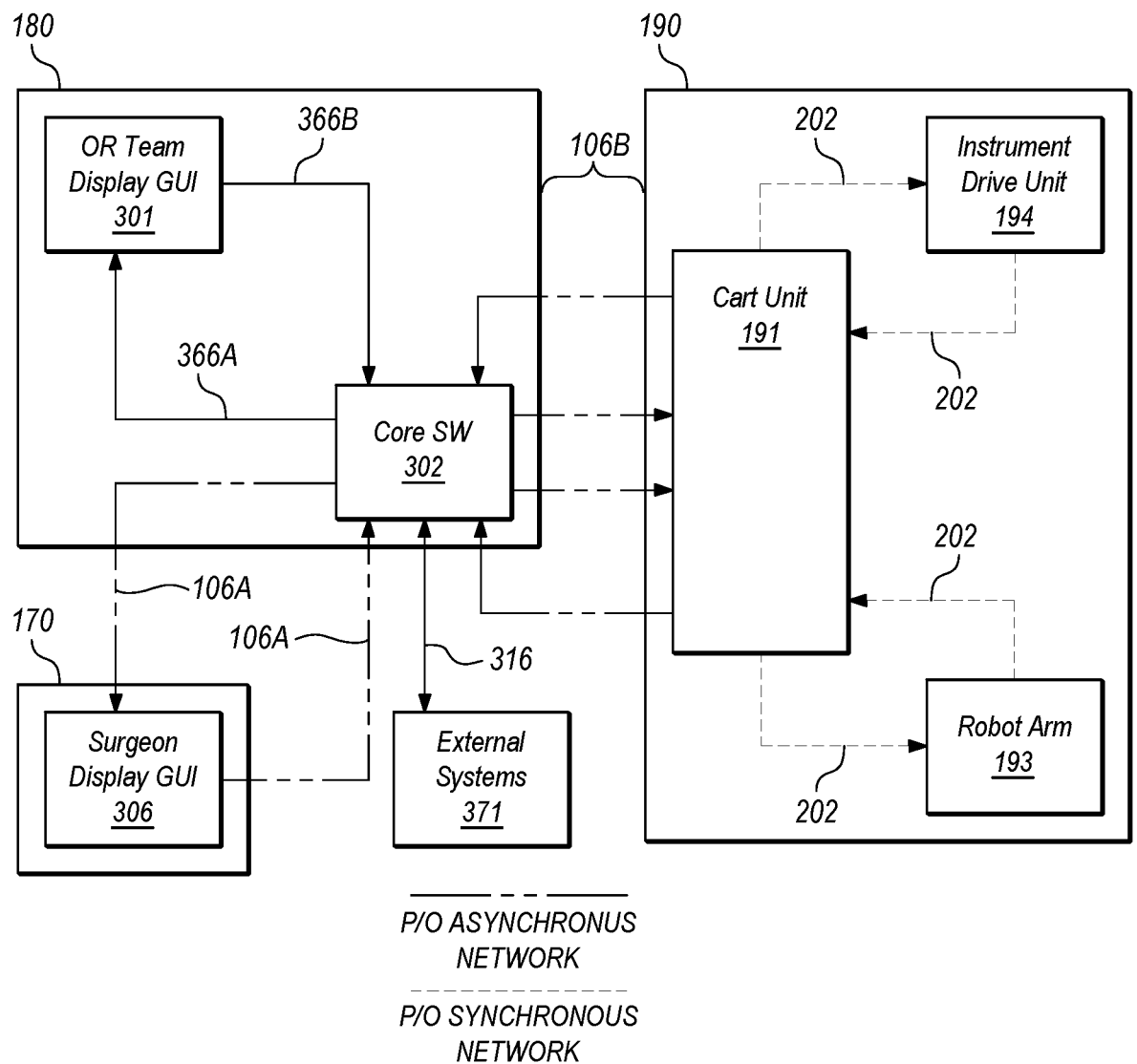
FIG. 3 is another schematic diagram illustrating an example configuration of the asynchronous network and the synchronous network of FIG. 2, which facilitates communication of various types of information among components of the robotic surgical system of FIG. 1, in accordance with an exemplary embodiment herein.

With reference to FIG. 3, various types of information communicated between the surgeon console 170, the networked computing node 180, the slave robot assembly 190, and external systems 371 are shown. As described above, the networked computing node 180 is communicatively coupled to the surgeon console 170 by way of the communication paths 106, and the slave robot assembly 190 and the surgeon console 170 are communicatively coupled with each other by way of the communication paths 106 and the networked computing node 180. Additionally, the networked computing node 180 is coupled to one or more external systems 371 by way of communication path 316.

Communication between the surgeon console 170 and the networked computing node 180 is effected by way of the asynchronous network defined at least in part by the surgeon console 170, the networked computing node 180, and communication paths 106a. Communication between the networked computing 180 and the cart unit 191 of the slave robot assembly 190 is effected by way of the asynchronous network defined at least in part by communication paths 106b. Communication between the cart unit 191 and other subunits of the slave robot assembly 190, such as the instrument drive unit 194 and/or the robot arm unit 193, is effectuated by way of the synchronous network defined at least in part by the communication paths 202. In some embodiments, the communication paths 202 are part of one ring network.

Examples of types of data transmitted to the networked computing node 180 from the surgeon console 170 by way of the communication paths 106a include, without limitation, data associated with various inputs from a surgeon, data associated with one or more sensors of the surgeon console 170, diagnostic data associated with the patient, state or mode data associated with the surgeon console, such as whether the surgeon console 170 is powered on or off, information about the surgeon, and configuration data associated with surgeon console 170, the networked computing node 180, and/or the slave robot assembly 190. The surgeon console 170 receives, from the networked computing node 180, haptic feedback in response to the interactions with one or more control units, such as the handles 112, of the surgeon console 170. Additionally, the surgeon console 170 receives data by way of the communication paths 106a from the networked computing node 180, including one or more images, such as captured by one or more image capturing devices, such as an endoscope, attached or coupled to an instrument drive unit of a slave robot assembly. The surgeon console 170 may also receive state or mode data and configuration data of various surgical instruments being used by the various slave robot assemblies and/or various other subunits of the system 100. The surgeon console 170 may also receive one or more commands from the networked computing node 180 for the surgeon console 170 to execute or for the surgeon operating the surgeon console to execute or follow. For example, the networked computing node 180 may transmit a command to the surgeon console 170 alerting the surgeon that a particular slave robot assembly is no longer functioning properly and that the surgeon should no longer attempt to use that slave robot assembly.

The networked computing node 180 is configured to update information presented to the OR team. For example, core software 302 may transmit updates to various views representing information relevant to the OR team on the OR team display GUI 301, by way of communication path 366a, in response to data received from surgeon console 170 and slave robot assemblies, such as slave robot assembly 190. Similarly, the core software 302 may receive certain data relevant to be transmitted to surgeon console 170 or slave robot assembly 190, by way of communication path 366b.

The networked computing node 180 is configured to transmit data to the cart unit 191 of the slave robot assembly 190 by way of communication paths 106b that are part of the asynchronous network and receive data from the cart unit 191 of the slave robot assembly 190 by way of the communication paths 106b. Examples types of data transmitted to the cart unit 191 by core software 302 of the networked computing node 180 include, without limitation, configuration data, operational state or mode data, and instructions or commands to perform certain actions for one or more the subunits 191, 192, 193, and 194 of the slave robot assembly 190.

The cart unit 191 of the slave robot assembly 190 transmits data received from the networked computing node 180 to the robot arm unit 193 and the instrument drive unit 194 by transmitting packets using communication paths such as 202 that are part of the synchronous network within the slave robot assembly 190. The cart unit 191 receives data from other subunits 192, 193, and/or 194 of the slave robot assembly 190 in a similar manner. For example, the cart unit 191 receives data related to sensors, positions, operational state or mode, and/or configuration from the instrument drive unit 194 and the robot arm unit 193 by way of the communication paths 202, as part of the synchronous network. For data that needs to be transmitted to the networked computing node 180, the cart unit 191 transmits the data using communication paths 106b that are part of the asynchronous network.

The networked computing node 180, in some examples, is communicatively coupled to one or more external systems 371. Examples of the external system 371 include, but are not limited to, patient systems, user systems, scheduling systems that schedules surgeries, medical procedure systems that can be used to reconfigure one or more set of rules, including local resolution rules and global resolution rules, used in making local and system wide decisions by surgical system 100 and other external systems. Examples of data received by the networked computing node 180 from the external systems 371 include, but are not limited to, pre-operation images, such as CT scans, etc., data related to the patient, including patient medical history, data related to the surgeons and staff. The networked computing node 180 may transmit to the external systems 371, data related to surgical instrument usage, surgeon console 170 usage, procedural data, and one or more images captured by image capturing devices utilized in the surgical system 100.

Figure 4:
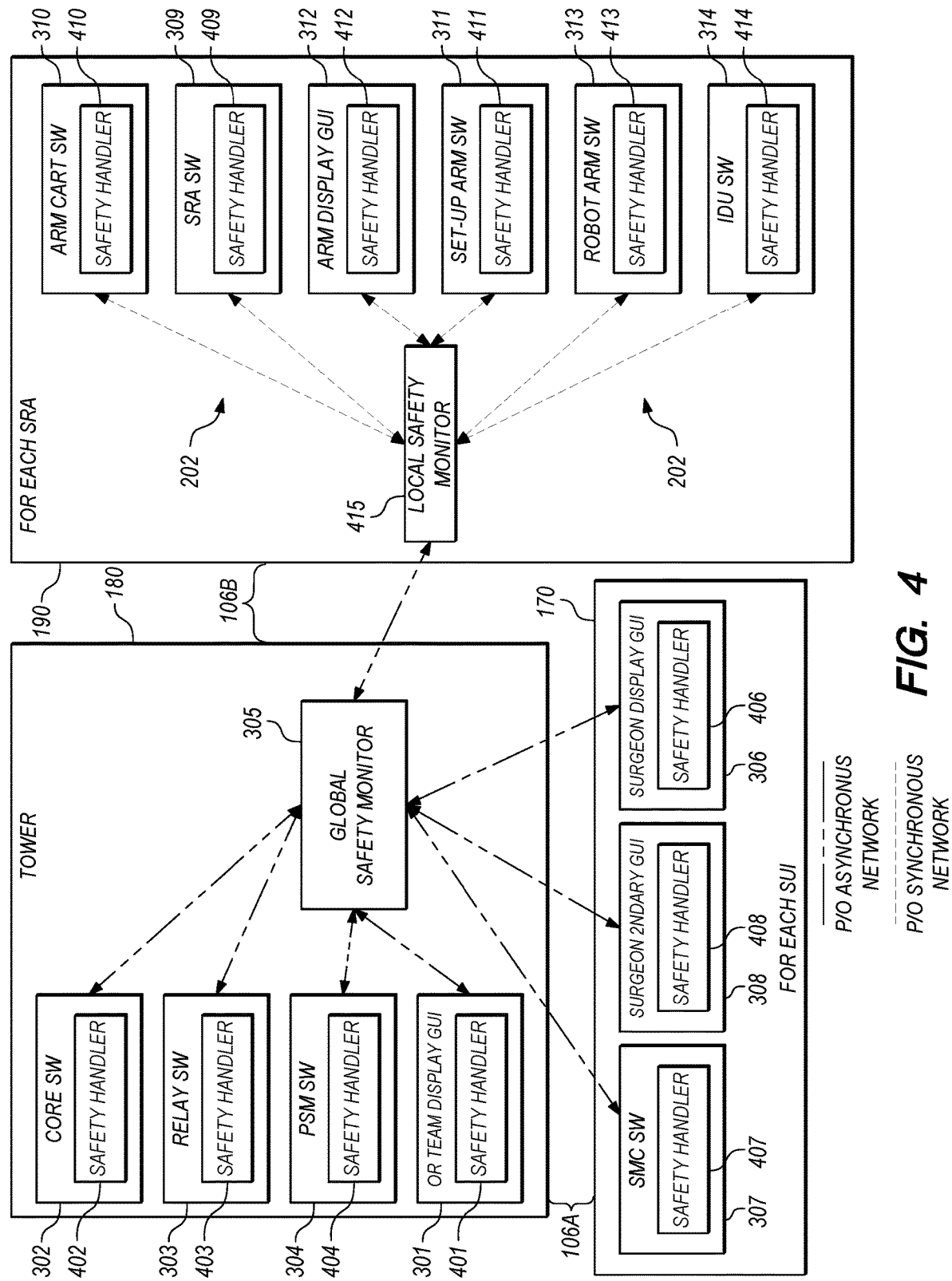
FIG. 4 is a schematic diagram showing a configuration of components of the robotic surgical system of FIG. 1, in which decision-making control is allocated among components of a slave robot assembly and/or of a networked computing node or other components, in accordance with an exemplary embodiment herein.

With reference to FIG. 4, there is shown an example configuration of components of the robotic surgical system 100, in which decision-making control is allocated among components of the slave robot assembly 190 and/or of the networked computing node 180 or another component. For the purpose of illustrating a clear example, various components of FIG. 1, FIG. 2, and FIG. 3 will be used to describe operations performed by the surgical system 100 in the context of FIG. 4.

Local decision-making, as described herein, refers to decisions made by a component, such as the slave robot assembly 190, that is not the master component of the system 100. Global decision-making, as described herein, refers to decisions made by the master component of the system 100, such as the networked computing node 180. As described above, the networked computing node 180 includes the global safety monitor 305, which includes one or more global resolution rules to identify various safety thresholds of system 100 and determine whether the various safety thresholds of system 100 have been breached. Thus, global decision-making may result in performing a global action, while local decision-making may result in performing a local action, as further described below. The global safety monitor 305 receives data related to various safety thresholds from various safety handlers in system 100, such as safety handlers 401, 402, 403, 404, 405, 406, 407, 408, 409, 410, 411, 412, 413, 414 (collectively, 401-414). Each safety handler 401-414 is configured to capture safety measurements and transmit the information to a decision-making unit, such as the global safety monitor 305 or the local safety monitor 415. Safety measurements, as described herein, may be performance measurements of different components of the system 100, and/or errors that occur during operation of a component of the system 100.

Each safety handler 401-414 is configured to capture safety measurements of a component or subsystem coupled to, and/or associated with, the safety handler 401-414. For example, safety handlers 401, 402, 403, 404, capture safety measurements of the graphical user interface 301, the core software system 302, the observer software system 303, the power supply management software system 304, respectively. Similarly, safety handlers 406, 407, 408 capture safety measurements of the graphical user interface 306, the sub-system 307, the graphical user interface 308, respectively, and safety handlers 409, 410, 411, 412, 413, 414 capture safety measurements of the slave robot assembly software sub-system 309, the cart software subsystem 310, the setup arm software subsystem 311, the arm display graphical user interface 312, the robot software sub-system 313, the instrument drive unit software sub-system 314.

As described above, safety measurements may be performance measurements of different components of the system 100, and/or errors that occur during operation of a component of the system 100 and safety handlers 401-414 transmit the information to a decision-making entity, such as the global safety monitor 305 or local safety monitor 415. For example, the safety handler 406 may capture whether a field on the graphical user interface of the display 122 of surgeon console 170 that should be editable, is editable when a user attempts to interact with the field, such as by clicking on the field, and transmits the whether the field is editable to the global safety monitor 305. If the data transmitted to the global safety monitor 305 indicates that the editable field fails to be editable and is preventing a user from editing the field, then the global safety monitor 305 may transmit an alert to the user at the surgeon console 170 and instruct the user to no longer consider the graphical user interface 306 to be a functioning graphical user interface.

Decision-making based on the information received from safety handlers 409-414 may be performed locally within a system of system 100 by a local decision making entity, the local safety monitor 415. The local safety monitor 415 is configured with one or more sets of local resolution rules to determine various instructions based on data received from safety handlers 409-414 and transmit instructions either to subunits 191, 192, 193, and 194 of the slave robot assembly 190 or to the global safety monitor 305 if the local safety monitor 415 is unable to resolve the safety issues, such as performance problems or errors. The local safety monitor 415 may generate an instruction based on comparing data received from safety handlers with safety threshold data included as part of the local resolution rules.

For example, the safety handler 413 coupled with the robot arm software sub-system 313 may transmit to the local safety monitor 415, information related to the amount of time the robot arm unit 193 takes to update the position of the robotic arm after the robot arm unit 193 receives instructions to update the position of the robotic arm. The local safety monitor 415 determines whether the amount of time the robot arm unit 193 took to update the position of the robotic arm after the robot arm unit 193 received instructions is greater than the safety threshold time for performance of such a movement by the robotic arm. If the amount of time is sufficiently greater than the safety threshold time, then the local safety monitor 415 may suspend or halt operation of robot arm unit 193 and transmit an alert to the global safety monitor 305 via the cart unit 191 to inform the global safety monitor 305 that the robot arm unit 193 of the slave robot assembly 190 is no longer operational. Thus, the slave robot assembly 190 in this example makes a decision locally.

However, if the amount of time is greater than the safety threshold but less than the amount of time sufficient for the local safety monitor 415 to halt or suspend operation of the robot arm unit 193, then the local safety monitor 415 may transmit an alert to the global safety monitor 305 via the cart unit 191 including the amount of time. The global safety monitor 305 may consider other safety measurements from other systems, such as the surgeon console 170, the networked computing node 180, in determining whether the amount of time is sufficient to halt or suspend operation of the robot arm unit 193. If the global safety monitor 305 determines that the amount of time in view of other safety measurements from other systems is sufficient to suspend or halt operation of the robot arm unit 193, then the networked computing node 180 transmits instructions to the slave robot assembly 190 to suspend or halt operation of the robot arm unit 193. Thus, the global safety monitor 305 makes a non-local or system-wide or global decision for slave robot assembly 190. In some embodiments, safety threshold data may be set and updated by one or more configuration procedures including from configuration data utilized during the configuration procedures. Safety threshold data may be updated based on updates to configuration data or other updates to various components of systems within system 100.

Figure 5:
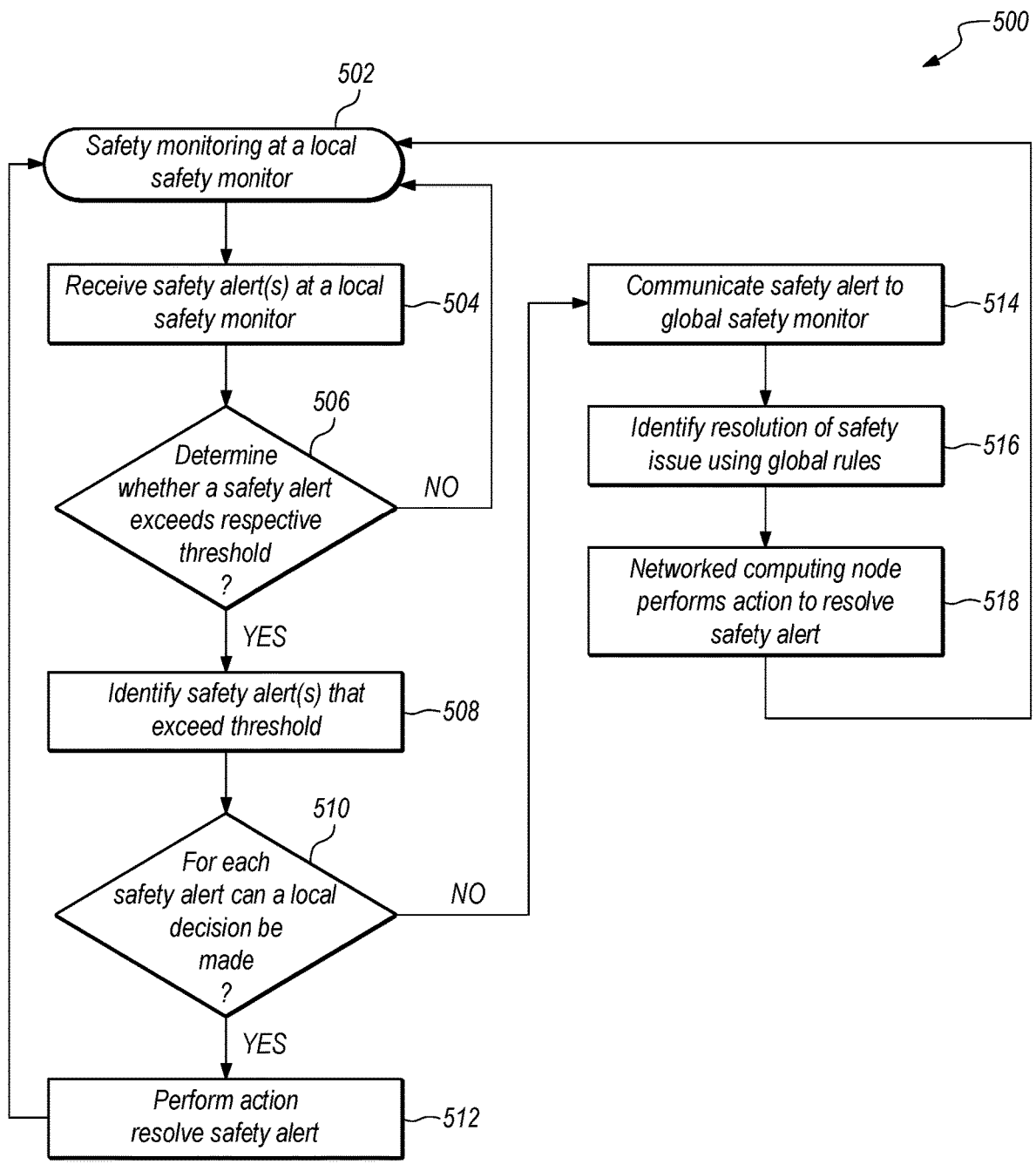
FIG. 5 is a flowchart that illustrates an example method of employing the configuration of the components of the surgical robotic system of FIG. 4 to allocate decision-making control among components of the slave robot assembly and/or of the networked computing node or other components, in accordance with an exemplary embodiment herein.

Turning now to FIG. 5, there is shown a method 500 of employing the configuration of the components of the surgical robotic system 100 to allocate decision-making control for safety related data among components of the slave robot assembly 190 and/or of the networked computing node 180 or other components. In step 502, a local safety monitor (such as the local safety monitor 415) is initiated and performs monitoring of various safety metrics of its corresponding slave robot assembly, such as the slave robot assembly 190. In step 504, the local safety monitor receives alerts from the various safety handlers (such as safety handlers 409-414) of subunits 191, 192, 193, and 194 of the slave robot assembly 190. The safety alerts may, in some examples, be periodically sent even if a particular safety issue has not occurred. For example, the robot arm unit 193 of the slave robot assembly 190 may transmit a safety alert to the local safety monitor every 30 seconds while the slave robot assembly is in operation, even if a particular safety issue has not occurred. In step 506, the local safety monitor determines whether any alert from the alerts received in step 504 exceed their respective thresholds. As described above in FIG. 4, the local safety monitor determines whether a corresponding threshold has been breached based on the rules associated with the safety monitoring. If no alert has exceeded the threshold, then the method 500 returns to step 502 and continues with the safety monitoring. If an alert exceeds corresponding threshold, then in step 508 the safety alert and the subunit that transmitted the safety alert is identified by the local safety monitor.

In step 510, for each safety alert that has been identified as exceeding its corresponding threshold, the local safety monitor, based on the rules associated with the thresholds of the various safety alerts, determines whether a local action can be performed by the local safety monitor. If a local action can be performed, then in step 512, the local safety monitor performs the local action to resolve the safety alert. If a local action cannot be performed, then in step 514, the local safety monitor communicates the safety alert to a global safety monitor (such as the global safety monitor 305). As described above, the global safety monitor resides in the networked computing node 180. In step 516, the global safety monitor identifies resolutions of the communicated safety alert using global safety rules. In step 518, the networked computing node 180 performs the actions necessary to resolve the received safety alert by determining instructions or commands for the subunit associated with the received safety alert and transmitting the instructions or commands to the cart unit of the slave robot assembly. The cart unit transmits the instructions or commands to the associated subunit of the slave robot assembly and to the local safety monitor. The local safety monitor may be configured to the mark that particular safety alert as resolved and resumes with the safety monitoring in step 502.

Figure 6:
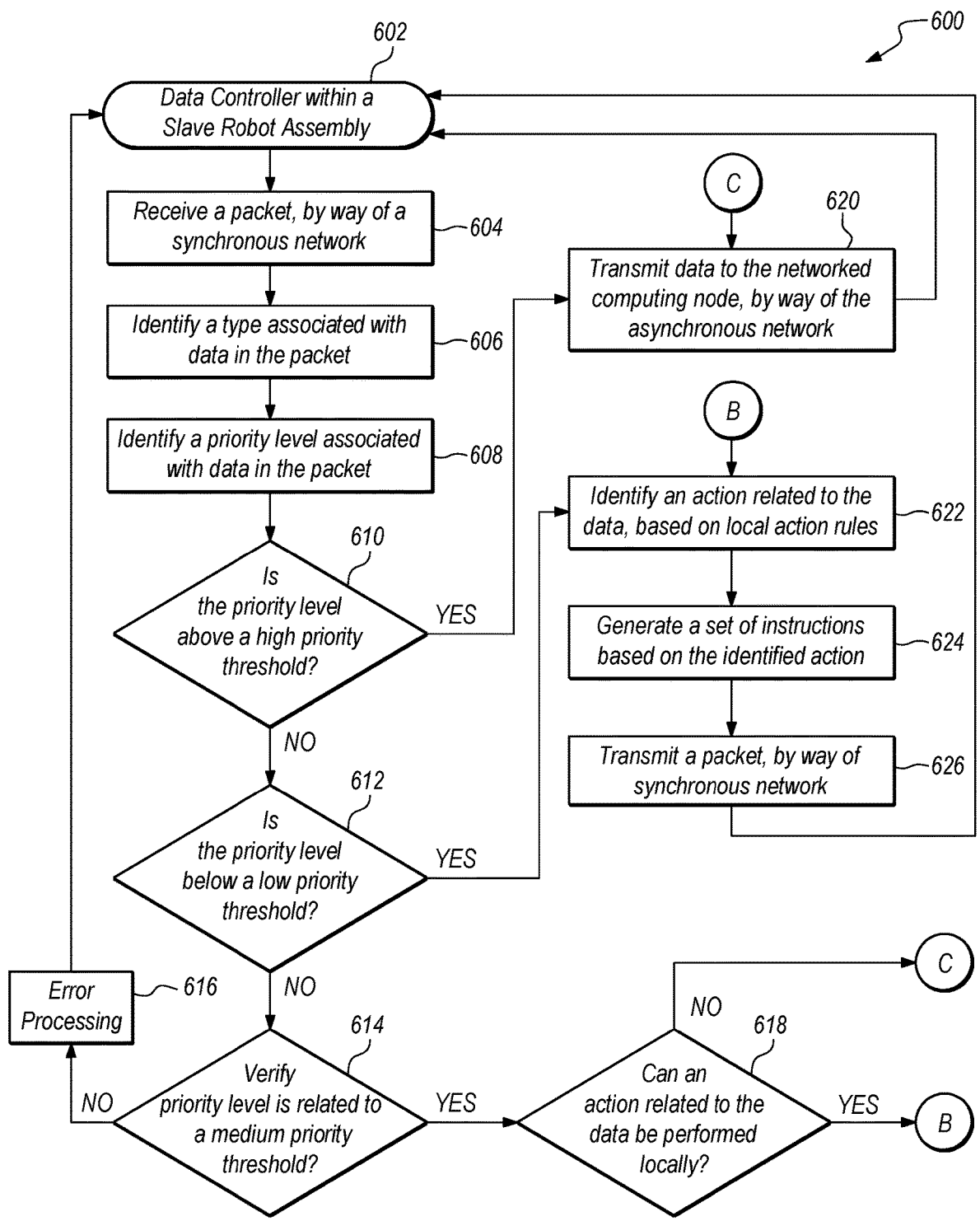
FIG. 6 is a flowchart that illustrates an example method of employing the configuration of the components of the surgical robotic system of FIG. 2 to allocate performance of an action, in accordance with an exemplary embodiment herein.

Turning now to FIG. 6, there is shown a method 600 of employing the configuration of the components of the surgical robotic system 100 to allocate performance of an action among components of the slave robot assembly 190 and/or of the networked computing node 180 or other components. For the purpose of illustrating a clear example, components described in the context of FIG. 2 will used in describing the method 600. In step 602, a data controller, such as the data controller 315, is initiated and monitors data received by the slave robot assembly software sub-system 309. In step 604, a packet is received by way of a synchronous network at the slave robot assembly software sub-system 309. In some embodiments, the slave robot software sub-system 309 is configured to transmit packets received by way of synchronous network to the data controller 315. In some embodiments, the data controller 315 simultaneously receives copies of the packets transmitted by way of synchronous network to the slave robot software sub-system 309. In step 606, the data controller 315 identifies a data type associated with the data in the packet. In some embodiments, the data controller 315 identifies the data type based on one or more rules configured to specify a data type based on an identifier of the data type. In step 608, the data controller 315 identifies a priority level associated with the data in the packet. As described above, the data controller 315 is configured to identify the priority level associated with the data in the packet based on the data type of the data in the packet.

In step 610, the data controller 315 determines whether the priority level associated with the data in the packet is above a high priority threshold. Examples of data associated with high priority include, but are not limited to, image data. In some embodiments, various priority levels are assigned different values and the high priority threshold is specified as a value that is slightly lower than the value assigned to the high priority level. If the data controller 315 determines that the priority level associated with the received data is above the high priority threshold, then in step 620, the data controller 315 transmits the data received in the packet to the networked computing node 180, by way of the asynchronous network. In some embodiments, the data controller 315 transmits an instruction to the slave robot assembly software sub-system 309 to transmit the data received in the packet and the slave robot assembly software sub-system 309 transmits the data to the networked computing node 180.

If the data controller 315 determines that the priority level associated with the received data is not above the high priority threshold, then in step 612, the data controller 315 determines whether the priority level associated with the data is below a low priority threshold. In some embodiments, the low priority threshold is specified as a value that is slightly higher than the value assigned to the low priority. If the data controller 315 determines that the priority level associated with the received data is below the low priority threshold, then the data controller 315, based on the local action rules and the priority level, identifies an action related to the data. In step 624, the data controller 315, performs the action as described above, and generates a set of instructions based on the action and in step 626, the data controller 315 transmits the packet, by way of the synchronous network, to a subunit of the slave robot assembly 190.

In step 612, if the data controller 315 determines that the priority level associated with the data is below the low priority threshold, then in step 614, the data controller 315 determines whether the priority level associated with the data is related to a medium priority threshold. In some embodiments, a medium priority threshold is assigned to a range of values, for example, a medium priority threshold will include all values lower than the value assigned to the high priority threshold and all values above the value assigned to the low priority threshold. A priority level is related to a medium priority threshold if the value of the priority level is within a range of values assigned to the medium priority threshold. If the priority level of the data is not related to the medium priority threshold, then in step 616, the data controller 315 identifies the packet as an error packet and performs error processing. Examples of the priority level of the data not related to the medium priority include, but are not limited to, the value in the packet being an unknown value, or corrupted, and/or the like. As part of the error processing, the data controller 315 identifies sender of the packet and transmits the error and the sender's information to the networked computing node 180. In some embodiments, the networked computing node 180, in response to receiving the error and the sender's information, transmits a message and/or instruction to the slave robot assembly 190 to restart the sender, or reload configuration data of the sender.

In step 614, if the data controller 315 determines that the priority level is related to a medium priority level, then data controller 315 determines whether an action related to the data can be performed locally. As described above, the data controller 315 determines whether an action related to the data can be performed locally based on the priority level associated with the data, the data type associated with the data, and the local action rules. If the local action rules specify that an action for the data cannot be performed locally, then the method 600 progresses to step 620 and the data controller 315 transmits the data to the networked computing node 180, by way of the asynchronous network. If the local action rules specify that an action can be performed locally, the method 600 progresses to step 622, and the data controller 315 performs according to steps 622, 624, and 626, describe above.

The phrases "in an example," "in examples," "in some examples," "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A surgical robotic system, comprising:
   a networked computing node;
   a slave robot assembly, including a plurality of subunits;
   a plurality of first communication paths; and
   a plurality of second communication paths,
   wherein the plurality of subunits are communicatively coupled to one another by way of the plurality of first communication paths, thereby forming at least a portion of a synchronous network,
   wherein the networked computing node and at least one of the plurality of subunits are communicatively coupled to one another by way of one or more of the plurality of second communication paths, thereby forming at least a portion of a second network, and are configured to communicate one or more packets to one another by way of the second network,
   wherein the at least one of the plurality of subunits is configured to communicate, with other ones of the plurality of subunits by way of the synchronous network, data from the one or more packets,
   wherein a clock rate of the synchronous network is not synchronized to a clock rate of the second network,
   wherein the networked computing node further includes a global safety monitor, the slave robot assembly includes a memory that stores one or more local resolution rules, and the at least one of the plurality of subunits is further configured to:
      receive a safety alert from another subunit of the plurality of subunits, by way of one or more of the plurality of first communication paths;
      determine whether a safety metric of the received safety alert exceeds a respective threshold;
      in response to determining that the safety metric exceeds the respective threshold, determine, based on the one or more local resolution rules, whether an action relating to the corresponding safety alert can be performed by one or more of the plurality of subunits;
      in response to determining that the action relating to the corresponding safety alert can be performed by one or more of the plurality of subunits, cause the action to be performed by one or more of the plurality of subunits to address the safety alert; and
      in response to determining that the action relating to the corresponding safety alert cannot be performed by any of the plurality of subunits, transmit, by way of the second network, the safety alert to the global safety monitor.

2. The surgical robotic system of claim 1, wherein the one or more local resolution rules include at least one of information indicating one or more actions corresponding to safety alerts, respectively, or information indicating whether one or more of the plurality of subunits of the slave robot assembly can perform the one or more actions corresponding to the safety alerts, respectively.

3. The surgical robotic system of claim 1, wherein the action includes powering down one or more of the plurality of subunits that are associated with the safety alert.

4. The surgical robotic system of claim 1, wherein the global safety monitor of the networked computing node is further configured to:
   receive the safety alert from the one of the plurality of subunits by way of one or more of the plurality of second communication paths; and
   in response to the receiving of the safety alert, cause the networked computing node to perform the action to address the safety alert.

5. The surgical robotic system of claim 1, wherein each of the plurality of subunits is configured to transmit a corresponding safety alert to the global safety monitor by way of a respective path including at least one of (a) the one or more of the plurality of second communication paths or (b) one or more of the plurality of first communication paths, another one of the plurality of subunits, and the one or more of the plurality of second communication paths.

6. The surgical robotic system of claim 1, further comprising:
   a surgeon console,
   wherein the surgeon console, the networked computing node, and the at least one of the plurality of subunits are communicatively coupled to one another by way of one or more of the plurality of second communication paths, thereby forming at least another portion of the second network.

7. The surgical robotic system of claim 1, wherein the plurality of subunits are communicatively coupled to each other, by way of the plurality of first communication paths, in a ring topology.

8. The surgical robotic system of claim 1, further comprising:
   a second slave robot assembly, including a plurality of second subunits; and
   a plurality of third communication paths,
   wherein the plurality of second subunits are communicatively coupled to one another by way of the plurality of third communication paths, thereby forming at least a portion of a second synchronous network, and
   wherein a clock rate of the second synchronous network is independent from the clock rate of the synchronous network and from the clock rate of the second network.

9. The surgical robotic system of claim 8, wherein the slave robot assembly is associated with a first unique identifier and the second slave robot assembly is associated with a second unique identifier.

10. The surgical robotic system of claim 9, wherein the one or more packets include the first unique identifier associated with the slave robot assembly or the second unique identifier associated with the second slave robot assembly.

11. The surgical robotic system of claim 1, wherein the second network is a synchronous network.

12. The surgical robotic system of claim 1, wherein the second network is an asynchronous network.

13. A method of employing a synchronous network and an asynchronous network of a surgical robotic system, the method comprising:
   storing one or more local resolution rules in a memory of a slave robot assembly;
   receiving, by at least one of a plurality of subunits of the slave robot assembly, a safety alert from another subunit of the plurality of subunits, by way of the synchronous network;
   determining whether a safety metric of the received safety alert exceeds a respective threshold;
   in response to determining that the safety metric exceeds the respective threshold, determining, based on the one or more local resolution rules, whether an action relating to the corresponding safety alert can be performed by one or more of the plurality of subunits;
   in response to determining that the action relating to the corresponding safety alert can be performed by one or more of the plurality of subunits, causing the action to be performed by one or more of the plurality of subunits to address the safety alert; and
   in response to determining that the action relating to the corresponding safety alert cannot be performed by any of the plurality of subunits, transmitting, by way of the asynchronous network, the safety alert to a global safety monitor in a networked computing node, wherein a clock rate of the synchronous network is not synchronized to a clock rate of the asynchronous network.

14. The method of claim 13, wherein the one or more local resolution rules include information indicating one or more actions corresponding to safety alerts, and/or information indicating whether one or more of the subunits of the slave robot assembly can perform the one or more actions corresponding to the safety alerts.

15. The method of claim 13, wherein the action includes powering down one or more of the plurality of subunits that are associated with the safety alert.

16. The method of claim 13, further comprising:
   receiving the safety alert from the one of the subunits by way of the asynchronous network, and, in response to the receiving of the safety alert, causing the networked computing node to perform the action to address the safety alert.

17. The method of claim 13, wherein transmitting, by way of the asynchronous network, the safety alert to the global safety monitor in the networked computing node includes transmitting by way of a respective path including at least one of (a) one or more of first communication paths of the asynchronous network or (b) one or more of second communication paths of the synchronous network, another one of the subunits, and the one or more of the first communication paths of the asynchronous network.

18. The method of claim 13, wherein the action includes inhibiting motors of one or more of the plurality of subunits that are associated with the safety alert.

* * * * *